US009387834B2

(12) United States Patent
Gordon

(10) Patent No.: US 9,387,834 B2
(45) Date of Patent: Jul. 12, 2016

(54) STEERING AND BRAKE CONTROL SYSTEM FOR VEHICLES

(71) Applicant: Scott Gordon, Tugun QLD (AU)

(72) Inventor: Scott Gordon, Tugun QLD (AU)

(73) Assignee: Next Generation Mobility PTY LTD, Tugun (AU)

( * ) Notice: Subject to any disclaimer, the term of this patent is extended or adjusted under 35 U.S.C. 154(b) by 132 days.

(21) Appl. No.: 14/311,203

(22) Filed: Jun. 20, 2014

(65) Prior Publication Data

US 2014/0373659 A1    Dec. 25, 2014

(30) Foreign Application Priority Data

Jun. 21, 2013   (AU) .................................. 2013902272

(51) Int. Cl.
| | | |
|---|---|---|
| *B62D 1/00* | (2006.01) | |
| *B60T 7/02* | (2006.01) | |
| *A61F 4/00* | (2006.01) | |
| *B62D 1/02* | (2006.01) | |
| *G05G 1/52* | (2008.04) | |

(52) U.S. Cl.
CPC ... *B60T 7/02* (2013.01); *A61F 4/00* (2013.01); *B62D 1/02* (2013.01); *G05G 1/52* (2013.01); *Y10T 74/20012* (2015.01)

(58) Field of Classification Search
CPC ............... B60T 7/02; B60T 7/08; B60T 7/10; B60T 7/101; A61F 4/00; G05G 1/08; G05G 1/52
See application file for complete search history.

(56) References Cited

U.S. PATENT DOCUMENTS

| | | | | | |
|---|---|---|---|---|---|
| 2,602,348 | A * | 7/1952 | Wilson | ................... | B60W 30/18 477/209 |
| 4,993,509 | A * | 2/1991 | Howell | ................. | B60W 30/18 180/315 |
| 5,129,492 | A * | 7/1992 | Lenz | .......................... | B60T 7/08 477/27 |
| 6,435,055 | B1 * | 8/2002 | Sato | .......................... | B60T 7/02 74/481 |
| 6,571,656 | B1 * | 6/2003 | Wells | ..................... | B60W 30/18 477/209 |
| 8,096,207 | B2 * | 1/2012 | Kazanchy | ................. | G05G 1/54 74/480 R |
| 2004/0129488 | A1 * | 7/2004 | Chernoff | ................ | B60K 41/28 180/333 |
| 2006/0118350 | A1 * | 6/2006 | Suyama | ..................... | B60T 7/02 180/332 |
| 2011/0154941 | A1 * | 6/2011 | Gibbs | ....................... | B60T 7/06 74/503 |

* cited by examiner

*Primary Examiner* — James English
(74) *Attorney, Agent, or Firm* — Weiner & Burt, P.C.; Irving M. Weiner; Pamela S. Burt

(57) ABSTRACT

The present invention relates to a combined steering and brake control system for vehicles and, in particular, to a mechanically combined steering and brake control system for use in safely controlling a vehicle configured for drivers with limited body movement, such as drivers having use of only one or no limbs. The invention further relates to a steering control system including a variable radius crank which enables the driver to select an appropriate crank radius. The invention further relates to a vehicle incorporating one or a combination of the control systems.

19 Claims, 3 Drawing Sheets

STEERING AND BRAKE CONTROL SYSTEM FOR VEHICLES

The present invention relates to a combined steering and brake control system for vehicles and, in particular, to a mechanically combined steering and brake control system for use in safely controlling a vehicle configured for drivers with limited body movement, such as drivers having use of only one or no limbs. The invention further relates to a steering control system including a variable radius crank which enables the driver to select an appropriate crank radius. The invention further relates to a vehicle incorporating one or a combination of the control systems.

BACKGROUND OF THE INVENTION

While vehicles having mechanically combined steering and brake systems are known, the Applicant is not aware of a vehicle with a mechanical steering/brake system that is particularly suited to drivers with significant physical impairment, such as drivers with use of one or no limbs, to safely control the vehicle. Adaptive systems for braking and steering involving electronics are known, but these are expensive to manufacture and often require the use of two active limbs. In addition, Government regulations and design rules in some countries specify that road vehicles employ only mechanical brake and steering systems.

Any discussion of documents, acts, materials, devices, articles or the like, which has been included in the present specification is solely for the purpose of providing a context for the present invention. It should not be taken as an admission that any or all of the previous discussion forms part of the prior art base or was common general knowledge in the field of the invention as it existed before the priority date of any of the claims herein.

SUMMARY OF THE INVENTION

In one aspect, the present invention provides a combined steering and brake control system for a vehicle having one or more wheels that are steerable by a wheel steering mechanism and whose rotary motion can be slowed or ceased by a wheel brake mechanism, the combined steering and brake control system including:
  a steering shaft including a sliding shaft component and a non-sliding shaft component aligned along a common longitudinal axis, wherein the non-sliding shaft component is operatively associated with said vehicle steering mechanism such that rotation of the non-sliding shaft component in one direction causes steer of the one or more wheels in one direction, and rotation of the non-sliding shaft component in an opposite direction causes steer of the one or more wheels in an opposite direction, wherein rotation of the sliding shaft component about said common axis translates to corresponding rotation of the non-sliding shaft component and linear movement of the sliding shaft component along said common axis does not translate to corresponding linear movement of the non-sliding shaft component; and
  a brake pin which is associated and moveable with said sliding shaft component and operatively associated with said wheel brake mechanism such that linear movement of the sliding shaft component along said common axis translates to corresponding linear movement of the brake pin in a direction along said common longitudinal axis from a rest position and causes said wheel brake mechanism to activate.

In an embodiment, the control system further includes:
  a control rod configured to be maneuvered using a single limb or mouth of a driver, said control rod being substantially aligned with said steering shaft along a parallel longitudinal axis and coupled thereto via a crank arm whose radius with respect to the steering shaft is adjustable by sliding of the crank arm along a transverse axis relative to the steering shaft, wherein rotation of the steering shaft is effected by moving said control rod along a substantially circular, radially disposed path about said longitudinal axis In an embodiment, movement of the sliding shaft component and brake pin is effected by moving the control rod along said common longitudinal axis.

In an embodiment, said control rod is connected to said crank arm via a ball and socket joint.

In an embodiment, said brake pin is biased in said rest position such that when a linear force causing said brake pin to move to thereby activate said wheel brake mechanism is no longer applied, the brake pin returns back to said rest position.

In an embodiment, said brake pin is at least partially housed inside a fixed casing within the vehicle, said fixed casing enclosing a spring for biasing said brake pin towards said rest position and at least one bearing unit for facilitating rotation of each of the sliding and non-sliding shaft components.

In an embodiment, said brake pin and spring are arranged such that movement of said brake pin away from its rest position involves pushing said slidable shaft component along said longitudinal axis.

In an alternative embodiment, said brake pin and spring are arranged such that movement of said brake pin away from its rest position involves pulling said slidable shaft component along said longitudinal axis.

In an embodiment, the wheel steering mechanism includes a linkage for linking the steering shaft to the one or more wheels and translating rotary motion of the steering shaft to turning motion of the one or more wheels.

In an embodiment, the linkage is flexible or collapsible.

In an embodiment, the linkage includes an inline reduction ratio.

In an embodiment, the wheel brake mechanism includes at least one push rod cable connecting the brake pin to a brake actuator associated with the at least one wheel.

In a still further aspect, the present invention provides a steering control system for a vehicle having one or more wheels that are steerable by a wheel steering mechanism, the steering control system including:
  a steering shaft operatively associated with said vehicle steering mechanism such that rotation of the shaft in one direction causes steer of the one or more wheels in one direction, and rotation of the shaft in an opposite direction causes steer of the one or more wheels in an opposite direction; and
  a control rod configured to be maneuvered using a single limb or mouth of a driver, said control rod being substantially aligned with said steering shaft along a parallel longitudinal axis when in use and coupled thereto via a crank arm whose radius with respect to the steering shaft is adjustable by sliding of the crank arm along a transverse axis relative to the steering shaft, wherein rotation of the steering shaft is effected by moving said control rod along a substantially circular, radially disposed path about said longitudinal axis.

In an embodiment, the steering shaft includes a sliding shaft component and a non-sliding shaft component aligned along a common longitudinal axis, wherein the non-sliding shaft component is operatively associated with said vehicle steering mechanism such that rotation of the non-sliding shaft component in one direction causes steer of the one or more wheels in one direction, and rotation of the non-sliding shaft component in an opposite direction causes steer of the one or more wheels in an opposite direction, wherein rotation of the sliding shaft component about said common axis translates to corresponding rotation of the non-sliding shaft component and linear movement of the sliding shaft component along said common axis does not translate to corresponding linear movement of the non-sliding shaft component.

In an embodiment, rotary motion of the one or more wheels can be slowed or ceased by a wheel brake mechanism, and the steering control system further includes a brake pin which is moveable with said sliding shaft component and operatively associated with said wheel brake mechanism such that linear movement of the brake pin in a direction along said common longitudinal axis from a rest position causes said wheel brake mechanism to activate.

In an embodiment, movement of the brake pin is effected by moving the control rod along said common longitudinal axis.

In an embodiment, said control rod is connected to said crank arm via a ball and socket joint.

In an embodiment, said brake pin is biased in said rest position such that when a linear force causing said brake pin to move to thereby activate said wheel brake mechanism is no longer applied, the brake pin returns back to said rest position.

In an embodiment, said brake pin is at least partially housed inside a fixed casing within the vehicle, said fixed casing enclosing a spring for biasing said brake pin towards said rest position and at least one bearing unit for facilitating rotation of each of the sliding and non-sliding shaft components.

In an embodiment, said brake pin and spring are arranged such that movement of said brake pin away from its rest position involves pushing said slidable shaft component along said longitudinal axis.

In an alternative embodiment, said brake pin and spring are arranged such that movement of said brake pin away from its rest position involves pulling said slidable shaft component along said longitudinal axis.

In an embodiment, the wheel steering mechanism includes a linkage for linking the steering shaft to the one or more wheels and translating rotary motion of the steering shaft to turning motion of the one or more wheels.

In an embodiment, the linkage is flexible or collapsible and the linkage includes an inline reduction ratio.

In an embodiment, the crank arm is slideable to different positions between a fully extended and a fully retracted position, wherein the fully extended position provides increased turning leverage than the fully retracted position.

In an embodiment, the wheel brake mechanism includes at least one cable push rod cable connecting the brake pin to a brake actuator associated with the at least one wheel.

In an embodiment, said control rod includes a gripping means at a driver end thereof to enable said driver to grip said driver using a limb or mouth. For example, the gripping means may be in the form of a mouthpiece.

In another aspect, the present invention provides a vehicle including a combined steering and brake control system as defined in preceding paragraphs.

BRIEF DESCRIPTION OF THE DRAWINGS

The present invention will now be described with reference to the accompanying drawings which illustrate exemplary embodiments of the present invention, wherein.

DETAILED DESCRIPTION OF EMBODIMENT(S) OF THE INVENTION

The following detailed description of the invention refers to the accompanying Figures. Although the description includes exemplary embodiments, other embodiments are possible, and changes may be made to the embodiments described without departing from the spirit and scope of the invention. Wherever possible, the same reference numbers are used throughout the embodiments and the following description to refer to the same and like parts.

Figure 1:
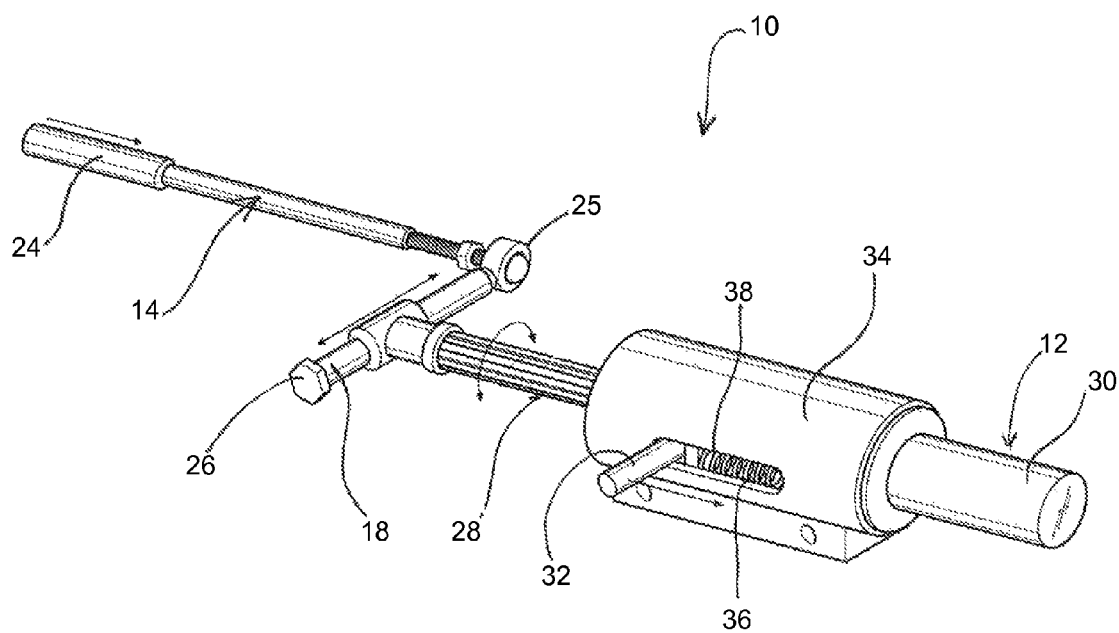
FIG. 1 is a rear perspective view of a combined steering and braking control system according to an embodiment.

FIG. 1 illustrates a device 10 which represents at least a steering control system according to an aspect of the invention. In particular, the device 10 may include a steering shaft 12 and a control rod 14 configured to be maneuvered using a single limb or mouth of a driver 16, the control rod 14 configured to be substantially aligned with the steering shaft 12 along a parallel longitudinal axis when in use. The control rod 14 may be coupled to the steering shaft 12 via a crank arm 18 whose radius with respect to the steering shaft 12 may be adjustable by sliding of the crank arm 18 along a transverse axis. This is shown, by way of example, in the three different configurations A, B and C shown in FIG. 2. The benefits of using an adjustable crank arm are outlined further below.

Figure 3:
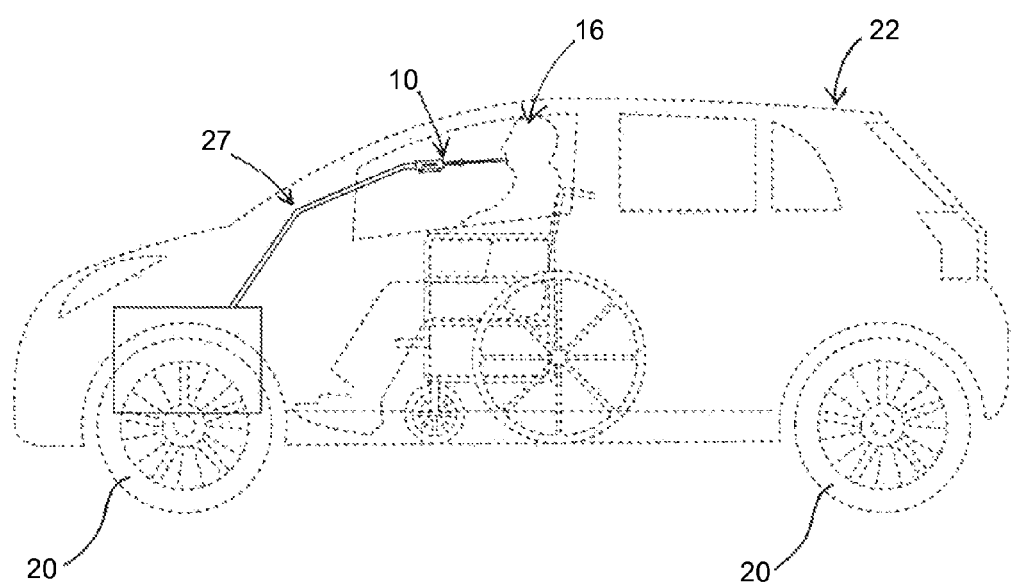
FIG. 3 is a side view of the combined steering and braking control system of FIG. 1 including an associated steering linkage in use inside a vehicle.

Movement of the control rod 14 along a circular path about the steering shaft axis causes rotation of the crank arm 18 and, in turn, rotation of the steering shaft 12. It is this motion which causes one or more wheels 20 of a vehicle 22 to turn or be steered in a direction dependent upon the direction of rotation. Such motion may be effected by a driver using a single active limb or, in the case of a driver having no active limbs, by appropriate movement of the driver's head/neck to guide the control rod 14 along a circular path whilst the control rod 14 is inserted in the driver's mouth, as shown in the embodiment of FIG. 3. In these circumstances, an appropriate gripping device 24 which may be a rubber tube (as shown) or a mouthpiece (not shown) may be incorporated into the tip of the control rod 14. In an embodiment, the control rod 14 is connected to crank arm 18 via a ball and socket joint 25 which allows for some movement of the control rod 14 with respect to the crank arm 18. The opposed end of the crank arm 18 may include a head 26 which ensures the control rod 14 does not slip out from its guide.

The present invention is not intended to be limited to any one vehicle steering mechanism which links the steering shaft 12 with the one or more wheels to translate rotary motion of the shaft 12 into steering of the one or more wheels in one of two directions. In an embodiment, this mechanism may be in the form of a linkage that may be flexible or collapsible in structure, and/or may include an inline reduction ratio to facilitate steering. However, alternative configurations may be possible. A linkage 27 according to an embodiment is shown in FIG. 3.

Figure 2:
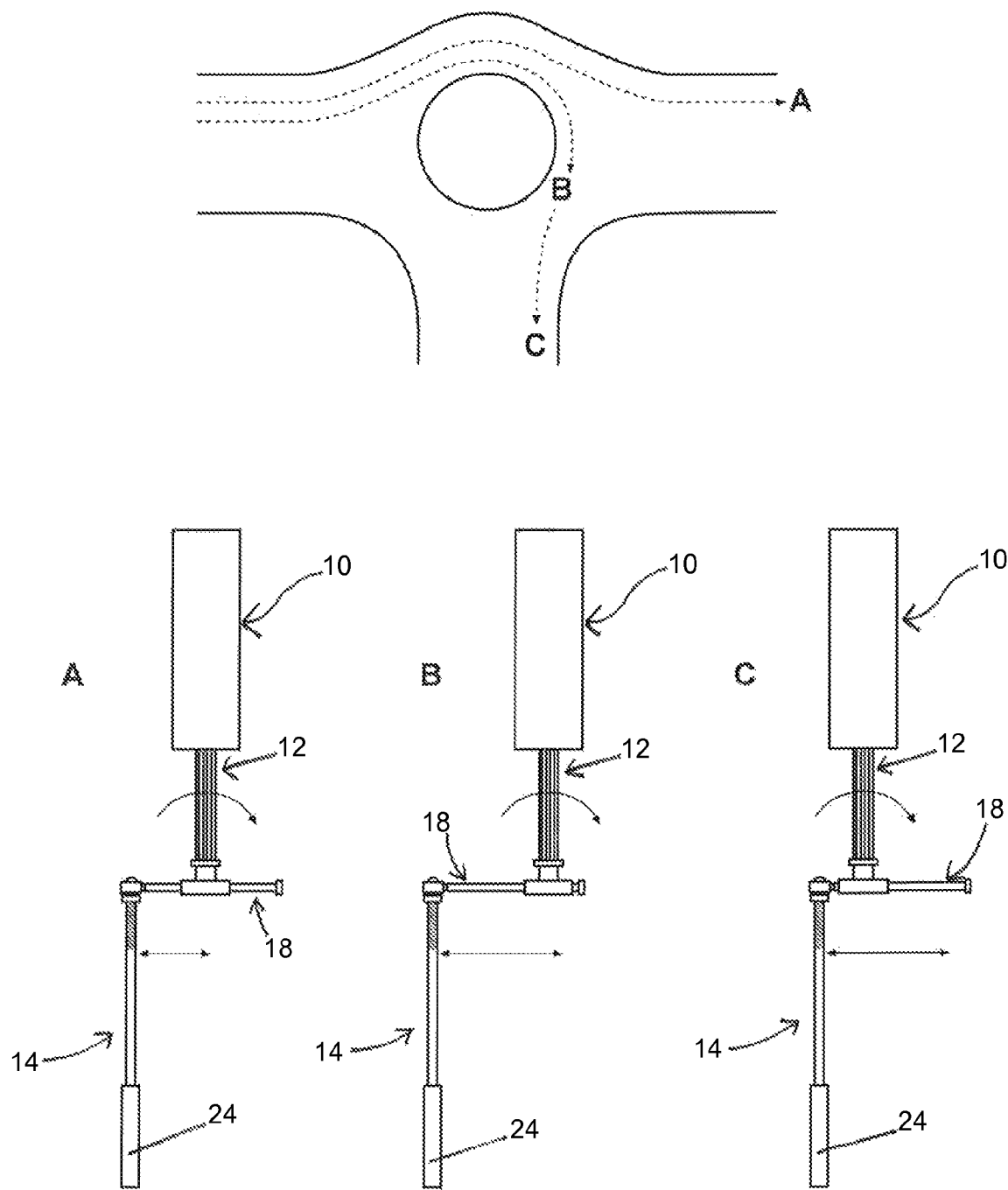
FIG. 2 is a diagrammatic representation of a roundabout intersection and an embodiment of a steering control system wherein three different crank arm radii are illustrated which correspond with the three different vehicle turning scenarios illustrated.

FIG. 2 illustrates the flexibility the steering device 10 provides with respect to navigating around different types of bends and corners. For example, path A represents a small turn required of a vehicle when travelling through a roundabout intersection. In this scenario, a driver may choose to shorten the radius of the crank arm 18 and thereby reduce the leverage required to effect turning of the vehicle. This turn could still be achieved when the arm is fully extended, but the device 10 at least provides the user with some level of control. Path B represents a 90 degree turn and, in this scenario, a driver may choose to maximize the radius of the crank arm 18 for maximum leverage. Path C signifies the point in the 90 degree turn where the driver will need to rotate the steering shaft 12 in an opposite direction back to its original position to re-commence straight driving. Minimizing the radius of the crank arm 18 at this point may ensure fast re-centering of the wheels and may be likened to a conventional steering wheel being allowed to slide through a driver's hands after performing a turn. Given that following a turn in one direction, the driver must turn in the opposite direction relatively quickly (depending on the speed of the vehicle), the less force required to effect a turn and the less movement of the head and neck to "straighten up" again, the easier the turning process is for the driver. Therefore, the variable radius crank arm allows the driver to find individual compromise between torque and speed.

The device 10 may also represent a combined steering and brake control system according to an aspect of the invention. The steering aspects have already been described, and now the braking control system is described.

The steering shaft 12 may be made up of sliding shaft component 28 and a non-sliding shaft component 30 aligned along a common longitudinal axis, wherein the non-sliding shaft component 30 is operatively associated with the vehicle steering mechanism (not shown) such that rotation of the non-sliding shaft component causes steer of the one or more wheels. The sliding and non-sliding shaft components may be linked such that rotation of the sliding shaft component 28 about said common axis translates to corresponding rotation of the non-sliding shaft component 30, but linear movement of the sliding shaft component 28 along said common axis does not translate to corresponding linear movement of the non-sliding shaft component 30.

Rotary motion of the one or more vehicle wheels may be configured to be slowed or ceased using an appropriate wheel brake mechanism (not shown) which may be operatively linked to a brake pin 32 associated and moveable with the sliding shaft component 28. Linear movement of the sliding shaft component 28 and hence the brake pin 32 in a direction along the common longitudinal axis may cause the wheel brake mechanism to activate. Accordingly, when a driver is driving the vehicle and wishes to slow or halt the vehicle, he or she may push the sliding shaft component 28 and hence the brake pin to effect braking of the wheels via whatever wheel brake mechanism is employed in the vehicle. Pushing the component 28 may be achieved using the control rod 14 which, as described earlier is also used for steering, by moving the control rod 14 along the common longitudinal axis in a pushing motion. In an alternate embodiment, the device 10 may be set up so that rather than pushing the component 28 to cause braking, pulling on this component 28 may cause braking.

In an embodiment, the brake pin 32 is at least partially housed inside a fixed casing 34 within the vehicle 22. In an embodiment where braking is achieved by pushing the component 28, the brake pin 32 is biased in a rest position adjacent the front of the easing. The reason for the pin 32 being biased is to ensure that when a linear force causing the brake pin 32 to move and thereby activate the wheel brake mechanism is no longer applied, the brake pin 32 returns back to its rest position. The fixed casing may enclose a spring 36 for biasing the brake pin towards its rest position, and at least one bearing unit (not shown) for accommodating and facilitating rotation of each of the sliding and non-sliding shaft components 28 and 30. In an embodiment, the brake pin 32 extends out of side windows 38 disposed on either side of the casing, as shown in FIG. 1. In an embodiment, the wheel brake mechanism is in the form of at least one push rod cable (not shown) connecting the brake pin 32 to a brake actuator (not shown) associated with the at least one wheel 20. In an embodiment, the vehicle 22 includes two such cables, one on each side extending to each wheel. It is to be understood however that other wheel brake mechanisms may be employed.

The skilled addressee would realize that the combined mechanical steering and braking system embodied in the present invention allows drivers with significant physical impairment to safely control a vehicle using head/neck movements (no active limbs) or using one active limb. Small movements in three dimensions can control the steering and braking in combination rather than in two separate movements (i.e. one for brake and another for steering). It is to be understood that other accessories could also be incorporated into the systems such as a squeeze-type hand brake (not shown) attached to the outside of the wheel crank.

Throughout this specification and claims which follow, unless the context requires otherwise, the word "comprise", and variations such as "comprises" and "comprising", will be understood to imply the inclusion of a stated integer or step, or group of integers or steps, but not the exclusion of any other integer or step or group of integers or steps.

The invention claimed is:

1. A combined steering and brake control system for a vehicle having one or more wheels that are steerable by a wheel steering mechanism and wherein rotary motion of the wheels can be slowed or ceased by a wheel brake mechanism, the combined steering and brake control system including:
   a steering shaft including a sliding shaft component and a non-sliding shaft component aligned along a common longitudinal axis, wherein the non-sliding shaft component is operatively associated with said vehicle steering mechanism such that rotation of the non-sliding shaft component in one direction causes steer of the one or more wheels in one direction, and rotation of the non-sliding shaft component in an opposite direction causes steer of the one or more wheels in an opposite direction, wherein rotation of the sliding shaft component about said common axis translates to corresponding rotation of the non-sliding shaft component and linear movement of the sliding shaft component along said common axis does not translate to corresponding linear movement of the non-sliding shaft component; and
   a brake pin which is associated and moveable with said sliding shaft component and operatively associated with said wheel brake mechanism such that linear movement of the sliding shaft component along said common axis translates to corresponding linear movement of the brake pin in a direction along said common longitudinal axis from a rest position and causes said wheel brake mechanism to activate.

2. The combined steering and brake control system of claim 1, further including:
   a control rod configured to be maneuvered using a single limb or mouth of a driver, said control rod being substantially aligned with said steering shaft along a parallel longitudinal axis and coupled thereto via a crank arm whose radius with respect to the steering shaft is adjustable by sliding of the crank arm along a transverse axis relative to the steering shaft, wherein rotation of the steering shaft is effected by moving said control rod along a substantially circular, radially disposed path about said longitudinal axis.

3. The combined steering and brake control system of claim 2 wherein movement of the sliding shaft component and brake pin is effected by moving the control rod along said common longitudinal axis.

4. The combined steering and brake control system of claim 3 wherein said control rod is connected to said crank arm via a ball and socket joint.

5. The combined steering and brake control system of claim 1 wherein said brake pin is biased in said rest position such that when a linear force causing said brake pin to move to thereby activate said wheel brake mechanism is no longer applied, the brake pin returns back to said rest position.

6. The combined steering and brake control system of claim 5 wherein said brake pin is at least partially housed inside a fixed casing within the vehicle, said fixed casing enclosing a spring for biasing said brake pin towards said rest position and at least one bearing unit for facilitating rotation of each of the sliding and non-sliding shaft components.

7. The combined steering and brake control system of claim 6 wherein said brake pin and spring are arranged such that movement of said brake pin away from said rest position involves pushing said slidable shaft component along said longitudinal axis.

8. The combined steering and brake control system of claim 7 wherein said brake pin and spring are arranged such that movement of said brake pin away from said rest position involves pulling said slidable shaft component along said longitudinal axis.

9. The combined steering and brake control system of claim 1 wherein the wheel steering mechanism includes a linkage for linking the steering shaft to the one or more wheels and translating rotary motion of the steering shaft to turning motion of the one or more wheels.

10. The combined steering and brake control system of claim 9 wherein the linkage is flexible or collapsible.

11. The combined steering and brake control system of claim 9 wherein the linkage includes an inline reduction ratio.

12. The combined steering and brake control system of claim 2 wherein said control rod includes a gripping means at a driver end thereof to enable said driver to grip said driver using a limb or mouth.

13. The vehicle of claim 1 including the combined steering and brake control system of claim 1.

14. A steering control system for a vehicle having one or more wheels that are steerable by a wheel steering mechanism, the steering control system including:
a steering shaft operatively associated with said vehicle steering mechanism such that rotation of the shaft in one direction causes steer of the one or more wheels in one direction, and rotation of the shaft in an opposite direction causes steer of the one or more wheels in an opposite direction; and
a control rod configured to be maneuvered using a single limb or mouth of a driver, said control rod being substantially aligned with said steering shaft along a parallel longitudinal axis when in use and coupled thereto via a crank arm whose radius with respect to the steering shaft is adjustable by sliding of the crank arm along a transverse axis relative to the steering shaft, wherein rotation of the steering shaft is effected by moving said control rod along a substantially circular, radially disposed path about said longitudinal axis.

15. The steering and control system of claim 14 wherein the crank arm is slideable to different positions between a fully extended and a fully retracted position, wherein the fully extended position provides increased turning leverage than the fully retracted position.

16. The steering control system of claim 14 wherein the wheel steering mechanism includes a linkage for linking the steering shaft to the one or more wheels and translating rotary motion of the steering shaft to turning motion of the one or more wheels.

17. The steering control system of claim 14 wherein the linkage is flexible or collapsible.

18. The steering control system of claim 14 wherein the linkage includes an inline reduction ratio.

19. The steering control system of claim 14 wherein said control rod includes a gripping means at a driver end thereof to enable said driver to grip said driver using a limb or mouth.

* * * * *